United States Patent [19]

Smith

[11] 4,113,962
[45] Sep. 12, 1978

[54] 5-OXA-13,14-DIDEHYDRO-11-DEOXY-17-PHENYL-18,19,20 TRINOR-PGE$_1$ COMPOUNDS

[75] Inventor: Herman W. Smith, Kalamazoo, Mich.

[73] Assignee: The Upjohn Company, Kalamazoo, Mich.

[21] Appl. No.: 820,976

[22] Filed: Aug. 1, 1977

Related U.S. Application Data

[62] Division of Ser. No. 657,740, Feb. 13, 1976.

[51] Int. Cl.$^2$ .......................................... C07C 177/00
[52] U.S. Cl. ...................................... 560/53; 560/121; 562/463
[58] Field of Search ........... 560/53; 260/520 R, 520 B

[56] References Cited
PUBLICATIONS

Derwent Abstract 4723U–B DT–2305044–Q, (Sep. 8, 1973).
Derwent Abstract 18176Y/11 BE 846-080, (Oct. 3, 1977).
Derwent Abstract 61891X/33 DT 2603-172, (May 8, 1976).
Derwent Abstract 59715X/32 BE 839-533, (Jan. 7, 1976).
Derwent Abstract 79219X/42 US 3,984,400, (May 10, 1976).

*Primary Examiner*—Paul J. Killos
*Attorney, Agent, or Firm*—Robert A. Armitage

[57] ABSTRACT

This invention comprises certain analogs of the prostaglandins in which the double bond between C-13 and C-14 is replaced by a triple bond. Also provided in this invention, are novel chemical processes and novel chemical intermediates useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

73 Claims, No Drawings

5-OXA-13,14-DIDEHYDRO-11-DEOXY-17-PHENYL-18,19,20 TRINOR-PGE₁ COMPOUNDS

The present application is a divisional application of Ser. No. 657,740, filed Feb. 13, 1976, now pending issuance as a U.S. Patent.

The present invention relates to prostaglandin analogs, for which the essential material constituting disclosure therefor is incorporated by reference here from Ser. No. 820,974, filed Aug. 1, 1977, which is a divisional application of Ser. No. 657,740.

I claim:

1. A prostaglandin analog of the formula

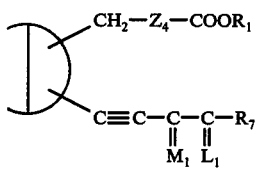

wherein

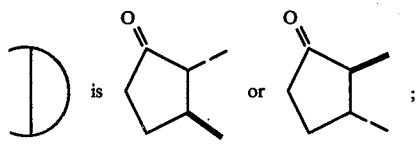

wherein $Z_4$ is $-CH_2-O-CH_2-(CH_2)_g-CH_2-$, $-(CH_2)_2-O-(CH_2)_g-CH_2-$, or $-(CH_2)_3-O-(CH_2)_g-$; wherein $g$ is one, 2, or 3; wherein $R_7$ is

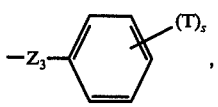

wherein $Z_3$ is oxa or methylene, $s$ is zero, one, 2, or 3, and T is chloro, fluoro, trifluoromethyl, alkyl of one to 3 carbon atoms, inclusive, or alkoxy of one to 3 carbon atoms, inclusive, the various T's being the same or different, with the proviso that not more than two T's are other than alkyl; wherein $L_1$ is

or a mixture of

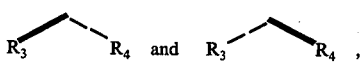

wherein $R_3$ and $R_4$ are hydrogen, methyl, or fluoro, being the same or different with the proviso that one of $R_3$ and $R_4$ is methyl only when the other is hydrogen or methyl, with the further proviso that one or both of $R_3$ and $R_4$ is fluoro only when $Z_3$ is methylene; wherein $M_1$ is

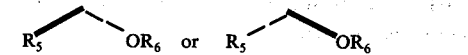

wherein $R_5$ and $R_6$ are hydrogen or methyl, with the proviso that one of $R_5$ and $R_6$ is methyl only when the other is hydrogen; and wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

2. A compound according to claim 1, wherein

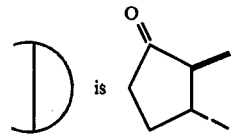

3. A compound according to claim 2, wherein $M_1$ is

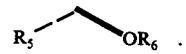

4. A compound according to claim 3, wherein $g$ is one.

5. A compound according to claim 4, wherein $R_3$, $R_4$, $R_5$, and $R_6$ are all hydrogen.

6. 15-epi-5-Oxa-13,14-didehydro-8β,12α-11-deoxy-17-phenyl-18,19,20-trinor-PGE₁, methyl ester, a compound according to claim 4.

7. A compound according to claim 2, wherein $M_1$ is

8. A compound according to claim 7, wherein $g$ is three.

9. A compound according to claim 7, wherein $g$ is one.

10. A compound according to claim 9, wherein $R_3$ and $R_4$ are both hydrogen.

11. A compound according to claim 10, wherein $R_5$ is methyl.

12. 5-Oxa-15-methyl-13,14-didehydro-8β,12α-11-deoxy-17-phenyl-18,19,20-trinor-PGE₁, a compound according to claim 11.

13. 5-Oxa-15-methyl-13,14-didehydro-8β,12α-deoxy-17-phenyl-18,19,20-trinor-PGE₁, methyl ester, a compound according to claim 11.

14. A compound according to claim 10, wherein $R_6$ is methyl.

15. 5-Oxa-13,14-didehydro-8β,12α-11-deoxy-17-phenyl-18,19,20-trinor-PGE₁, 15-methyl ether, a compound according to claim 14.

16. 5-Oxa-13,14-didehydro-8β,12α-11-deoxy-17-phenyl-18,19,20-trinor-PGE₁, methyl ester, 15-methyl ether, a compound according to claim 14.

17. A compound according to claim 10, wherein $R_5$ and $R_6$ are both hydrogen.

18. 5-Oxa-13,14-didehydro-8β,12α-11-deoxy-17-phenyl-18,19,20-trinor-PGE₁, a compound according to claim 17.

19. 5-Oxa-13,14-didehydro-8β,12α-11-deoxy-17-phenyl-18,19,20-trinor-PGE$_1$, methyl ester, a compound according to claim 17.

20. A compound according to claim 9, wherein at least one of R$_3$ and R$_4$ is methyl.

21. A compound according to claim 20, wherein R$_3$ and R$_4$ are both methyl.

22. A compound according to claim 21, wherein R$_5$ is methyl.

23. 5-Oxa-15,16,16-trimethyl-13,14-didehydro-8β,12α-11-deoxy-17-phenyl-18,19,20-trinor-PGE$_1$, methyl ester, a compound according to claim 22.

24. A compound according to claim 21, wherein R$_6$ is methyl.

25. 5-Oxa-16,16-dimethyl-13,14-didehydro-8β,12α-11-deoxy-17-phenyl-18,19,20-trinor-PGE$_1$, methyl ester, 15-methyl ether, a compound according to claim 24.

26. A compound according to claim 21, wherein R$_5$ and R$_6$ are both hydrogen.

27. 5-Oxa-16,16-dimethyl-13,14-didehydro-8β,12α-11-deoxy-17-phenyl-18,19,20-trinor-PGE$_1$, a compound according to claim 26.

28. 5-Oxa-16,16-dimethyl-13,14-didehydro-8β,12α-11-deoxy-17-phenyl-18,19,20-trinor-PGE$_1$, methyl ester, a compound according to claim 26.

29. A compound according to claim 9, wherein at least one of R$_3$ and R$_4$ is fluoro.

30. A compound according to claim 29, wherein R$_3$ and R$_4$ are both fluoro.

31. A compound according to claim 30, wherein R$_5$ is methyl.

32. 5-Oxa-15-methyl-16,16-difluoro-13,14-didehydro-8β,12α-11-deoxy-17-phenyl-18,19,20-trinor-PGE$_1$, methyl ester, a compound according to claim 31.

33. A compound according to claim 30, wherein R$_6$ is methyl.

34. 5-Oxa-16,16-difluoro-13,14-didehydro-8β,12α-11-deoxy-17-phenyl-18,19,20-trinor-PGE$_1$, methyl ester, 15-methyl ether, a compound according to claim 33.

35. A compound according to claim 30, wherein R$_5$ and R$_6$ are both hydrogen.

36. 5-Oxa-16,16-difluoro-13,14-didehydro-8β,12α-11-deoxy-17-phenyl-18,19,20-trinor-PGE$_1$, a compound according to claim 35.

37. 5-Oxa-16,16-difluoro-13,14-didehydro-8β,12α-11-deoxy-17-phenyl-18,19,20-trinor-PGE$_1$, methyl ester, a compound according to claim 35.

38. A compound according to claim 1, wherein

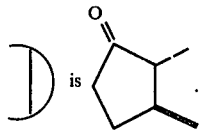

39. A compound according to claim 38, wherein M$_1$ is

40. A compound according to claim 39, wherein g is one.

41. A compound according to claim 40, wherein R$_3$, R$_4$, R$_5$, and R$_6$ are all hydrogen.

42. 15-epi-5-Oxa-13,14-didehydro-11-deoxy-17-phenyl-18,19,20-trinor-PGE$_1$, methyl ester, a compound according to claim 41.

43. A compound according to claim 38, wherein M$_1$ is

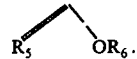

44. A compound according to claim 43, wherein g is three.

45. A compound according to claim 43, wherein g is one.

46. A compound according to claim 45, wherein R$_3$ and R$_4$ are both hydrogen.

47. A compound according to claim 46, wherein R$_5$ is methyl.

48. 5-Oxa-15-methyl-13,14-didehydro-11-deoxy-17-phenyl-18,19,20-trinor-PGE$_1$, a compound according to claim 47.

49. 5-Oxa-15-methyl-13,14-didehydro-11-deoxy-17-phenyl-18,19,20-trinor-PGE$_1$, methyl ester, a compound according to claim 47.

50. A compound according to claim 46, wherein R$_6$ is methyl.

51. 5-Oxa-13,14-didehydro-11-deoxy-17-phenyl-18,19,20-trinor-PGE$_1$, 15-methyl ether, a compound according to claim 50.

52. 5-Oxa-13,14-didehydro-11-deoxy-17-phenyl-18,19,20-trinor-PGE$_1$, methyl ester, 15-methyl ether, a compound according to claim 50.

53. A compound according to claim 46, wherein R$_5$ and R$_6$ are both hydrogen.

54. 5-Oxa-13,14-didehydro-11-deoxy-17-phenyl-18,19,20-trinor-PGE$_1$, a compound according to claim 53.

55. 5-Oxa-13,14-didehydro-11-deoxy-17-phenyl-18,19,20-trinor-PGE$_1$, methyl ester, a compound according to claim 53.

56. A compound according to claim 45, wherein at least one of R$_3$ and R$_4$ is methyl.

57. A compound according to claim 56, wherein R$_3$ and R$_4$ are both methyl.

58. A compound according to claim 57, wherein R$_5$ is methyl.

59. 5-Oxa-15,16,16-trimethyl-13,14-didehydro-11-deoxy-17-phenyl-18,19,20-trinor-PGE$_1$, methyl ester, a compound according to claim 58.

60. A compound according to claim 57, wherein R$_6$ is methyl.

61. 5-Oxa-16,16-dimethyl-13,14-didehydro-11-deoxy-17-phenyl-18,19,20-trinor-PGE$_1$, methyl ester, 15-methyl ether, a compound according to claim 60.

62. A compound according to claim 57, wherein R$_5$ and R$_6$ are both hydrogen.

63. 5-Oxa-16,16-dimethyl-13,14-didehydro-11-deoxy-17-phenyl-18,19,20-trinor-PGE$_1$, a compound according to claim 62.

64. 5-Oxa-16,16-dimethyl-13,14-didehydro-11-deoxy-17-phenyl-18,19,20-trinor-PGE$_1$, methyl ester, a compound according to claim 62.

65. A compound according to claim 45, wherein at least one of R$_3$ and R$_4$ is fluoro.

66. A compound according to claim 65, wherein R$_3$ and R$_4$ are both fluoro.

67. A compound according to claim 66, wherein R$_5$ is methyl.

68. 5-Oxa-15-methyl-16,16-difluoro-13,14-didehydro-11-deoxy-17-phenyl-18,19,20-trinor-PGE$_1$, methyl ester, a compound according to claim 67.

69. A compound according to claim 66, wherein R$_6$ is methyl.

70. 5-Oxa-16,16-difluoro-13,14-didehydro-11-deoxy-17-phenyl-18,19,20-trinor-PGE$_1$, methyl ester, 15-methyl ether, a compound according to claim 69.

71. A compound according to claim 66, wherein R$_5$ and R$_6$ are both hydrogen.

72. 5-Oxa-16,16-difluoro-13,14-didehydro-11-deoxy-17-phenyl-18,19,20-trinor-PGE$_1$, a compound according to claim 71.

73. 5-Oxa-16,16-difluoro-13,14-didehydro-11-deoxy-17-phenyl-18,19,20-trinor-PGE$_1$, methyl ester, a compound according to claim 71.

* * * * *

UNITED STATES PATENT OFFICE
CERTIFICATE OF CORRECTION

Patent No. 4,113,962     Dated September 12, 1978

Inventor(s) Herman W. Smith

It is certified that error appears in the above-identified patent and that said Letters Patent are hereby corrected as shown below:

Column 1, line 12, "filed August 1, 1977," should read -- filed August 1, 1977, now U.S. Patent 4,099,015, --.

*Signed and Sealed this*

*Thirteenth* Day of *February 1979*

[SEAL]

Attest:

RUTH C. MASON
*Attesting Officer*

DONALD W. BANNER
*Commissioner of Patents and Trademarks*